United States Patent
Truong et al.

(10) Patent No.: US 11,413,212 B2
(45) Date of Patent: Aug. 16, 2022

(54) ENERGY REGENERATING END EFFECTOR, AND ASSOCIATED SYSTEMS AND METHODS

(71) Applicant: L'Oreal, Paris (FR)

(72) Inventors: Lily Truong, Seattle, WA (US); Wayne Weber, Federal Way, WA (US)

(73) Assignee: L'Oreal, Paris (FR)

( * ) Notice: Subject to any disclaimer, the term of this patent is extended or adjusted under 35 U.S.C. 154(b) by 819 days.

(21) Appl. No.: 16/262,743

(22) Filed: Jan. 30, 2019

(65) Prior Publication Data
US 2020/0237604 A1 Jul. 30, 2020

(51) Int. Cl.
*A61H 7/00* (2006.01)
*A61H 23/02* (2006.01)
*A61N 5/06* (2006.01)

(52) U.S. Cl.
CPC ......... *A61H 7/005* (2013.01); *A61H 23/0218* (2013.01); *A61N 5/0616* (2013.01); *A61H 2201/1207* (2013.01); *A61N 2005/0652* (2013.01)

(58) Field of Classification Search
CPC .............. A61H 23/0218; A61H 7/005; A61H 2201/1207; A46B 5/0012; A46B 15/0026; A46B 15/0034; A46B 2200/1006; A46B 2200/102; A46B 13/023; A46B 13/026; A61N 2005/0652
See application file for complete search history.

(56) References Cited

U.S. PATENT DOCUMENTS 6,032,313 A * 3/2000 Tsang .................... A46B 13/02
 15/21.1
6,249,706 B1 * 6/2001 Sobota .................. A61N 1/326
 606/41

(Continued)

FOREIGN PATENT DOCUMENTS

| EP | 3391793 A1 | 10/2018 |
|---|---|---|
| WO | 2004026077 A1 | 4/2004 |
| WO | 2005006538 A1 | 1/2005 |

OTHER PUBLICATIONS

Invitation to Pay Additional Fees and Communication Relating to the Results of the Partial International Search, dated May 14, 2020, issued in corresponding International Application No. PCT/US2020/014116, filed Jan. 17, 2020, 15 pages.

(Continued)

*Primary Examiner* — Justine R Yu
*Assistant Examiner* — Kelsey E Baller
(74) *Attorney, Agent, or Firm* — Christensen O'Connor Johnson Kindness PLLC

(57) ABSTRACT

A skincare device having energy regenerating end effector is presented. In one embodiment, an end effector includes an inner end effector structure configured to oscillate about an axis. The inner end effector structure includes at least one magnet and a plurality of contacting elements configured to contact skin of a user. The end effector also includes an outer end effector structure having at least one induction coil. The at least one magnet and the at least one induction coil cooperate to generate electrical current in the at least one induction coil when the end effector oscillates about the axis.

20 Claims, 7 Drawing Sheets

CROSS-SECTION A-A

(56) References Cited

U.S. PATENT DOCUMENTS

| | | | | |
|---|---|---|---|---|
| 6,838,794 | B2* | 1/2005 | Iwamoto | F16C 9/02 |
| | | | | 310/168 |
| 7,386,906 | B2* | 6/2008 | Roth | A46B 13/06 |
| | | | | 15/28 |
| 9,386,843 | B2 | 7/2016 | Grez et al. | |
| 10,327,980 | B1* | 6/2019 | Termanini | A61N 1/00 |
| 2004/0191729 | A1* | 9/2004 | Altshuler | A61F 7/00 |
| | | | | 433/215 |
| 2006/0175909 | A1* | 8/2006 | Kraus | B26B 19/282 |
| | | | | 310/12.04 |
| 2007/0142845 | A1* | 6/2007 | Akridge | B26B 19/38 |
| | | | | 606/131 |
| 2009/0177125 | A1* | 7/2009 | Pilcher | A46B 15/0034 |
| | | | | 601/18 |
| 2015/0202114 | A1* | 7/2015 | Pardoel | A61H 7/005 |
| | | | | 601/112 |

OTHER PUBLICATIONS

International Search Report and Written Opinion, dated Jul. 6, 2020, issued in corresponding International Application No. PCT/US2020/014116, filed Jan. 17, 2020, 19 pages.

* cited by examiner

CROSS-SECTION B-B

ENERGY REGENERATING END EFFECTOR, AND ASSOCIATED SYSTEMS AND METHODS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, an end effector includes an inner end effector structure configured to oscillate about a first axis. The inner end effector structure includes at least one magnet and a plurality of contacting elements configured to contact skin of a user. The end effector includes an outer end effector structure having at least one induction coil. The at least one magnet and the at least one induction coil cooperate to generate electrical current in the at least one induction coil when the end effector structure oscillates about an axis.

In one aspect, the inner end effector structure is configured to oscillate with first oscillations about the axis, and the outer end effector structure is configured to oscillate with second oscillations about the axis.

In one aspect, the first oscillations of the inner end effector structure are generated by an oscillating shaft of the end effector, and the second oscillations of the outer end effector structure are generated at least in part by electromagnetic interactions between the at least one magnet and the at least one induction coil.

In another aspect, the first oscillations of the inner end effector structure and the second oscillations of the outer end effector structure are directed in opposite directions at least at some times during the operation of the end effector, and wherein the electrical current in the at least one induction coil increases with increased relative velocity between the at least one magnet of the inner end effector structure and the at least one induction coil of the outer end effector structure.

In one aspect, the end effector also includes a regulator configured to regulate voltage of the induction coil into a charging voltage of an energy storage device carried by the end effector structure. In one aspect, the energy storage device is a capacitor. In another aspect, the energy storage device is a rechargeable battery.

In one aspect, the end effector also includes an electrical device configured to receive electrical current from the energy storage device. In another aspect, the electrical device is configured to generate at least one of light, ultrasound, audible sound and heat toward the skin of the user. In one aspect, the electrical device is a light emitting diode (LED) configured to generate light toward the skin of the user.

In one aspect, the plurality of contacting elements of the inner end effector structure is a first plurality of contacting elements, and the outer end effector structure includes a second plurality of contacting elements configured to contact the skin of the user.

In one aspect, the end effector is a part of a skincare device, the skincare device further includes a handle connected with the end effector, where the handle includes: an electrical motor configured to impart oscillatory motion on an oscillating shaft connected with the inner end effector structure; and a battery configured to power the electrical motor.

In one embodiment, an end effector includes: an inner end effector structure configured to oscillate about an axis. The inner end effector structure includes at least one induction coil and a plurality of contacting elements configured to contact skin of a user, and an outer end effector structure includes at least one magnet. The at least one induction coil and the at least one magnet cooperate to generate electrical current in the at least one induction coil.

In one aspect, the inner end effector structure is configured to oscillate with first oscillations about the axis, and the outer end effector structure is configured to oscillate with second oscillations about the axis. In another aspect, the first oscillations of the inner end effector structure are generated by an oscillating shaft of the end effector, and the second oscillations of the outer end effector structure are generated at least in part by electromagnetic interactions between the at least one magnet and the at least one induction coil.

In one aspect, the plurality of contacting elements of the inner end effector structure is a first plurality of bristles, and the outer end effector structure includes a second plurality of bristles configured to contact the skin of the user.

In one aspect, the end effector includes a regulator configured to regulate voltage of the induction coil into a charging voltage of an energy storage device carried by the end effector structure. In one aspect, the energy storage device is a capacitor or a rechargeable battery.

In one aspect, the end effector also includes an electrical device configured to receive electrical current from the energy storage device, where the electrical device is configured to generate at least one of light, ultrasound, audible sound and heat toward the skin of the user.

In one aspect, the end effector is a part of a skincare device, and the skincare device also includes a handle connected with the end effector. The handle includes: an electrical motor configured to impart oscillatory motion on an oscillating shaft connected with the inner end effector structure; and a battery configured to power the electrical motor.

In one embodiment, an end effector includes: an inner end effector structure configured to oscillate about an axis, where the inner end effector structure comprises at least one magnet; and an outer end effector structure. The outer end effector structure includes: at least one induction coil, and a plurality of electrical devices configured to affect skin of a user. The at least one induction coil and the at least one magnet cooperate to generate electrical current in the at least one induction coil, and the electrical current at least partially powers the plurality of electrical devices.

In one embodiment, the inner end effector structure is configured to oscillate with first oscillations about the axis, and the outer end effector structure is configured to oscillate with second oscillations about the axis. In one aspect, the first oscillations of the inner end effector structure are generated by an oscillating shaft of the end effector, and the second oscillations of the outer end effector structure are generated at least in part by electromagnetic interactions between the at least one magnet and the at least one induction coil.

In one embodiment, the plurality of electrical devices is a first plurality of electrical devices, the inner end effector structure comprises a second plurality of electrical devices configured to affect the skin of the user, and the electrical current at least partially powers the second plurality of electrical devices. In one aspect, the first plurality of electrical devices and the second plurality of electrical devices comprise light emitting diodes (LEDs).

DESCRIPTION OF THE DRAWINGS

The foregoing aspects and the attendant advantages of the inventive technology will become more readily appreciated as the same become better understood by reference to the following detailed description, when taken in conjunction with the accompanying drawings, wherein.

DETAILED DESCRIPTION

The following disclosure describes energy regenerating end effectors, and associated systems and methods. A person skilled in the relevant art will also understand that the technology may have additional embodiments, and that the technology may be practiced without several of the details of the embodiments described below with reference to FIGS. 1-5.

Briefly described, skincare devices with energy regenerating end effectors are described herein. In some embodiments, a skincare device includes an end effector having an inner end effector structure and an outer end effector structure. The inner end effector structure (e.g., an inner brush head or an inner elastomeric portion) may carry one or more magnets, and the outer part (e.g., an outer brush head or an outer elastomeric portion) may carry one or more induction coils. When the inner end effector structure and the outer end effector structure of the end effector move relative to each other, for example, through oscillations, a travel of the induction coils through the magnetic field of the magnets induces electrical current in the induction coils. This current may be harvested into a storage element (e.g., a capacitor or a rechargeable battery) that, in turn, can power auxiliary devices of the end effector (e.g., light emitting diodes, sources of heat, sources of sound or ultrasound, etc.). These auxiliary device may be powered solely from the storage element, or from the storage element in conjunction with the main source of power (e.g., a battery in the handle of the skincare device). In some embodiments, the storage element may be lighter and smaller than the main source of power.

In some embodiments, the end effector structure (also referred to as the inner part) of the end effector is driven by an oscillating shaft connected to an electrical motor. The outer end effector structure (also referred to as the outer part) of the end effector may oscillate independently of the inner end effector structure. This relative motion of the inner part with respect to the outer part generates electrical current in the skincare device. In different embodiments, charging of the storage element is regulated by electrical networks that include one or more controllers, resistors, inductors, and/or other electrical components.

Figure 1:
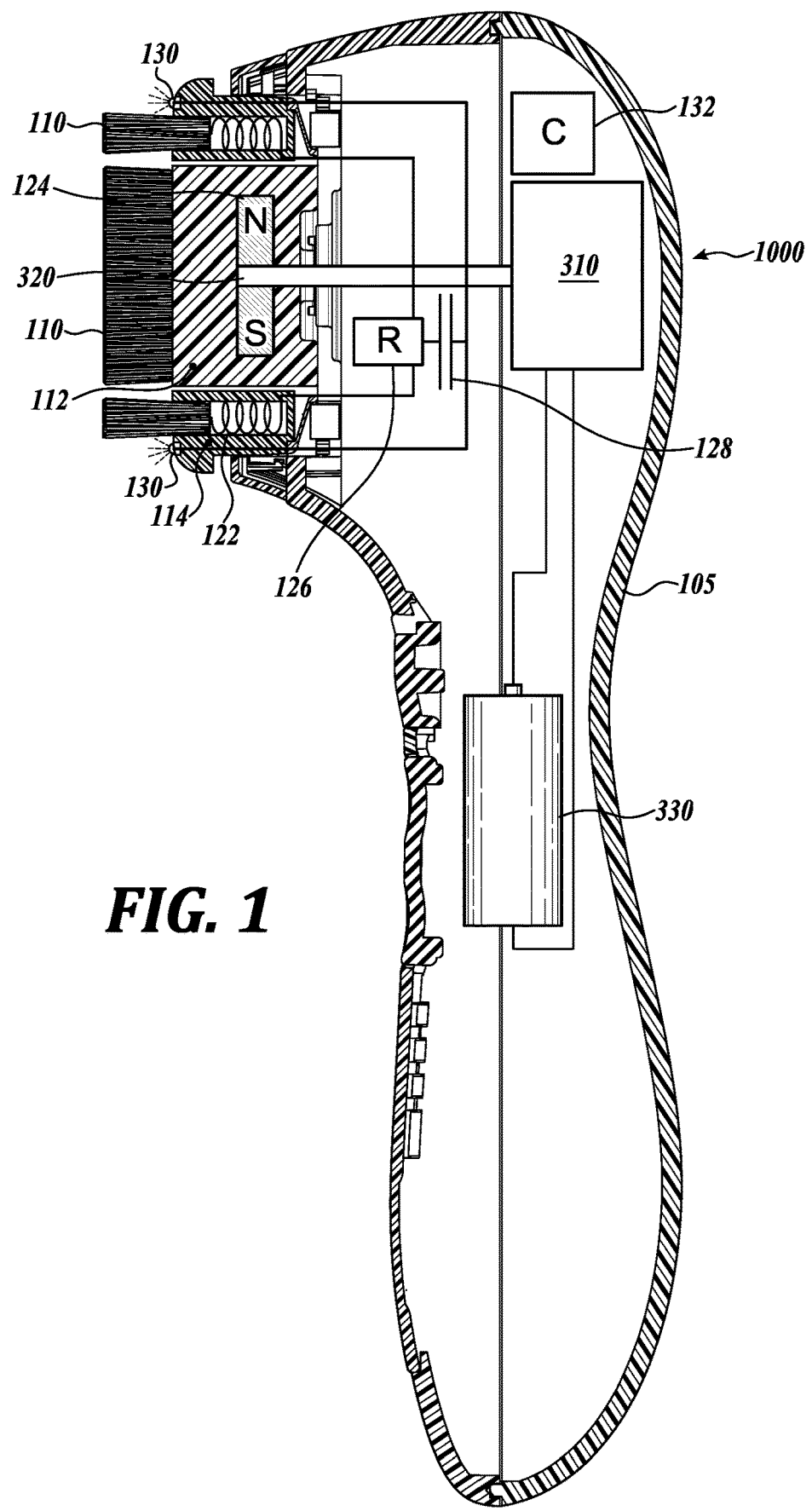
FIG. 1 is a cross-sectional side view of a skincare device in accordance with an embodiment of the present technology.

FIG. 1 is a cross-sectional side view of a skincare device 1000 in accordance with an embodiment of the present technology. The illustrated skincare device 1000 includes an inner end effector structure 112 (inner part or inner portion) and an outer end effector structure 114 (outer part or outer portion). The inner end effector structure 112 is actuated by a motor 310 through a shaft 320. In some embodiments, the motor 310 provides an oscillating motion to the inner end effector structure 112. The motor 310 may be energized by a battery 330.

In some embodiments, the outer end effector structure 114 is capable of independently oscillating about the inner end effector structure 112, without being driven by the motor 310 and shaft 320. For example, the outer end effector structure 114 may be mechanically disconnected from the inner end effector structure 112 and slideably linked to a housing 105 of the skincare device 1000, thus being free to oscillate about the inner end effector structure 112. In other embodiments, the outer end effector structure 114 may be fixed onto the housing 105 of the skincare device 1000, thus being fixed with respect to the oscillations of the inner end effector structure 112.

In some embodiments, the inner end effector structure 112 carries one or more magnets 124. As the inner end effector structure 112 is driven into oscillatory motion by the motor 310, the magnet 124 also oscillates about the shaft (axis) 320. In some embodiments, the outer end effector structure 114 carries one or more induction coils 122 that are subjected to an oscillatory magnetic field generated by the oscillations of the magnet 124. As a result, an electrical current is generated in the induction coils 122. This electrical current may be directed to an energy storage element 128 (e.g., a capacitor or a rechargeable battery). Therefore, the end effector 100 may be referred to as an energy regenerating end effector. Charging of the energy storage element 128 may be controlled by a controller (e.g., a processor or regulator) 132, one or more resistors 126, and/or other electrical elements. In different embodiments, the inner end effector structure 112 may carry the induction coils 122, while the output of the brush head 114 may carry one or more magnets.

In some embodiments, the energy stored in the energy storage element 128 may power auxiliary devices 130, for example, light emitting diodes (LEDs). In other embodiments, the auxiliary devices 130 may be sources of sound, sources of ultrasound, sources of heat, etc.

Figure 2:
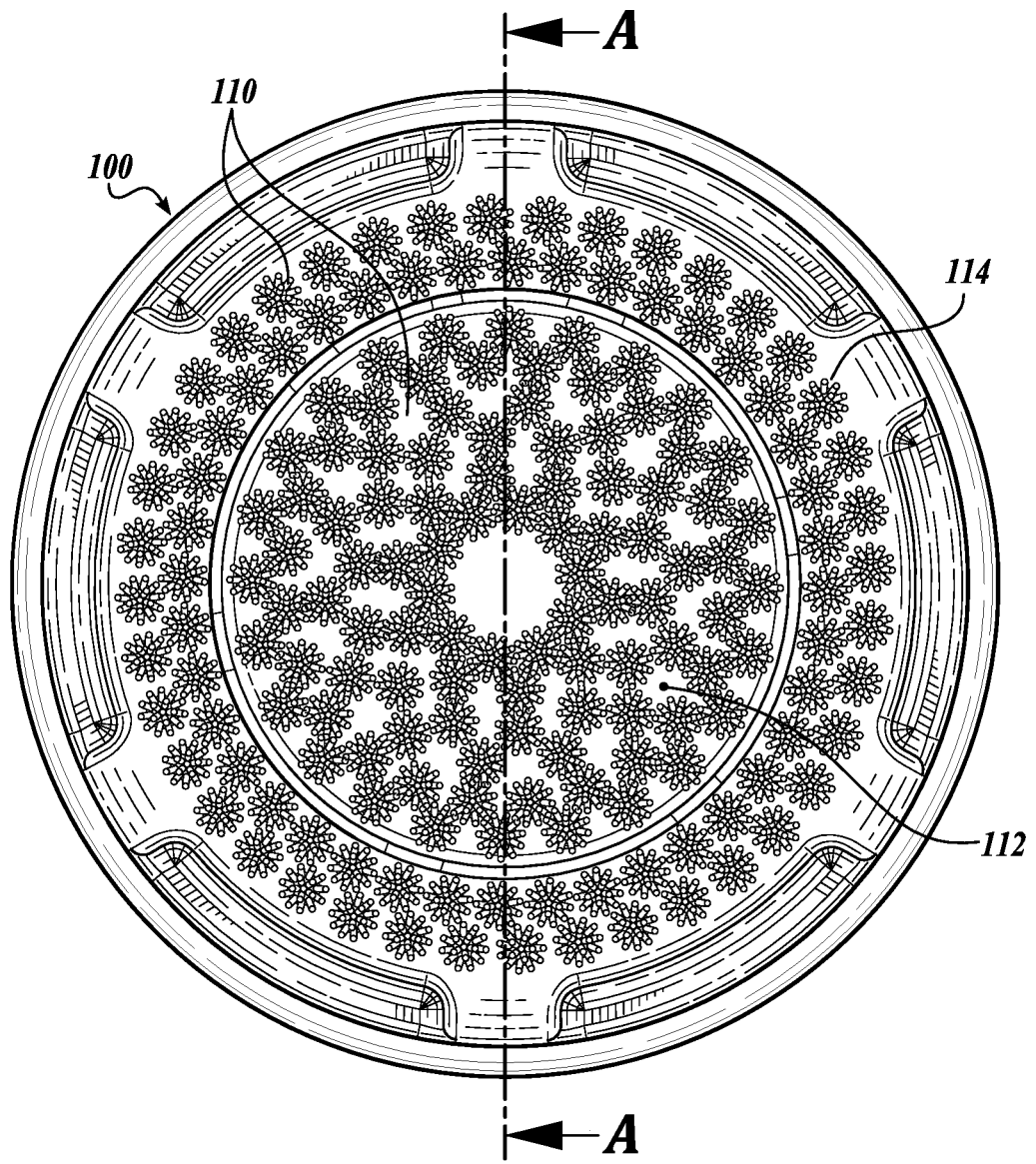
FIG. 2 is a front plan view of an end effector of the skincare device in accordance with an embodiment of the present technology.

FIG. 2 is a front plan view of an end effector 100 of the skincare device in accordance with an embodiment of the present technology. In the illustrated embodiment, both the inner end effector structure 112 and the outer end effector structure 114 carry bristles 110. However, in different embodiments one of the brush heads 112/114 may carry the bristles 110, or may carry, for example, elements for massaging skin of the user or other elastomeric elements for contacting skin of the user. These elements 110 are collectively referred to as the contacting elements 110.

Figure 2A:
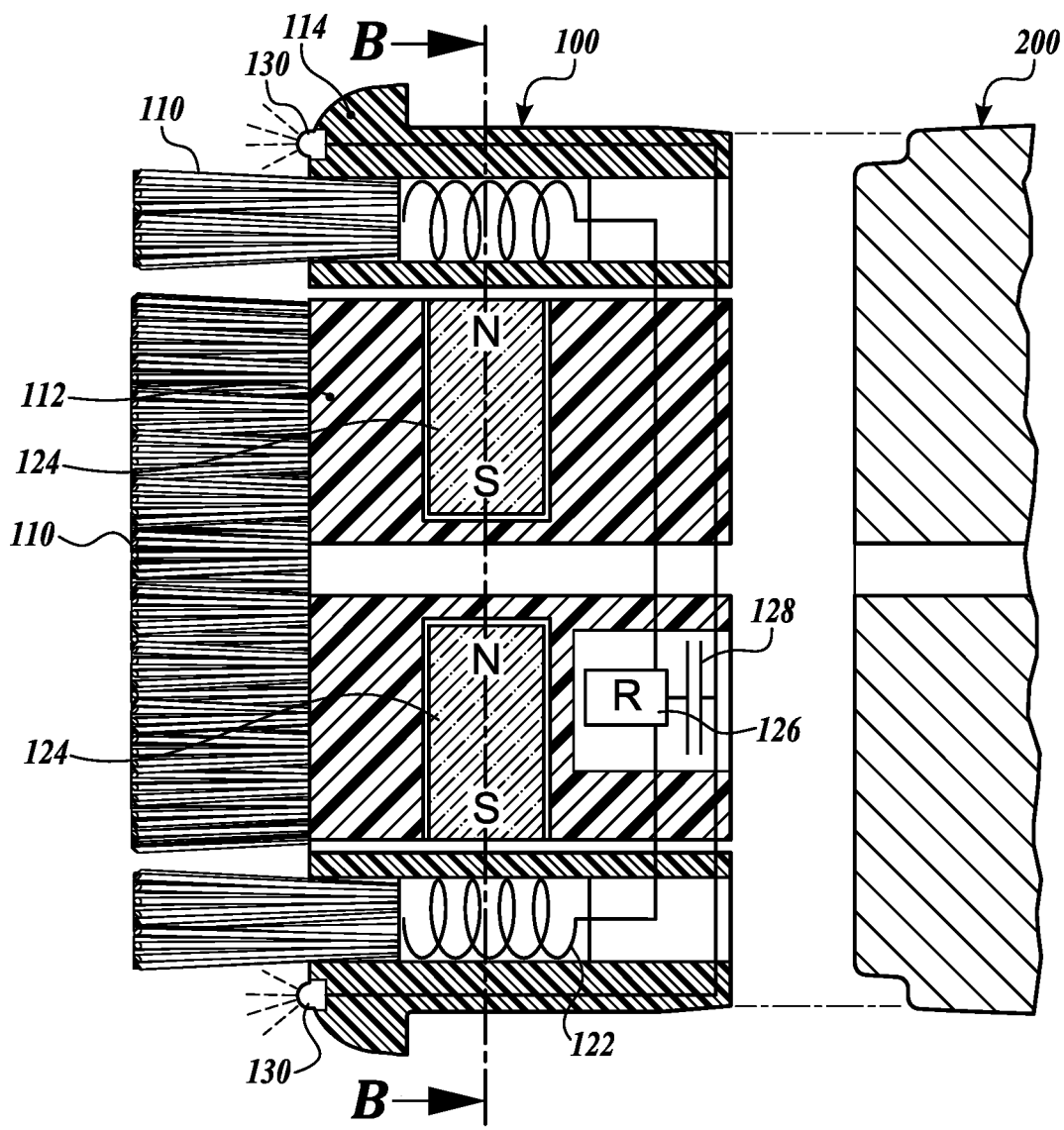
FIGS. 2A and 2B are cross-sectional views of the embodiments of the skincare device shown in FIG. 2.

FIG. 2A is a cross-sectional view A-A of the embodiments of the skincare device shown in FIG. 2. In some embodiments, the end effector 100 mates with a handle 200. In some embodiments, the inner end effector structure 112 carries multiple magnets 124, and the outer end effector structure 114 carries multiple induction coils 122. In other embodiments, the locations of the magnets and the induction coils may be switched.

Figure 2B:
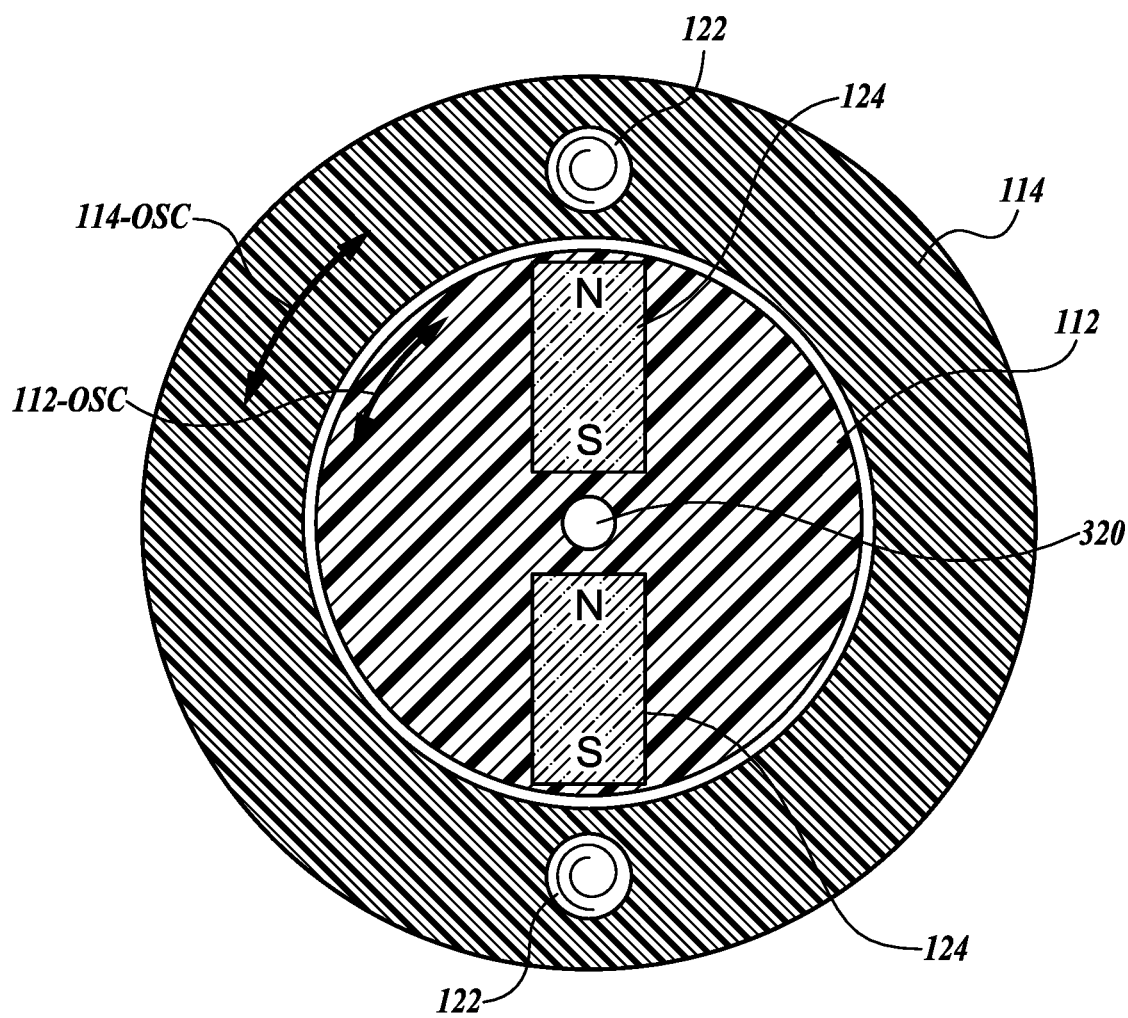

FIG. 2B is a cross-sectional view B-B of the embodiments of the skincare device shown in FIG. 2A. Oscillations of the inner end effector structure 112 are indicated as arrows 112-OSC, and oscillations of the outer end effector structure 114 are indicated as arrows 114-OSC. In some embodiments, oscillations of the inner end effector structure 112 are driven by the shaft 320 that is connected with the motor in the handle of the skincare device. In some embodiments, oscillations of the outer end effector structure 114 are driven by the electromagnetic forces exerted by the magnets 124 onto the induction coils 122 of the outer end effector structure 114. Without being bound to theory, it is believed that the additional oscillation of the outer end effector structure 114 may result in an increased relative velocity of the induction coils 122 with respect to the magnetic field of the magnets 124, thus increasing electrical current in the induction coils 122. In other embodiments, the outer end effector structure 114 may be fixed with respect to the shaft 320 by being fixed, for example, to the handle of the skincare device.

Figure 3:
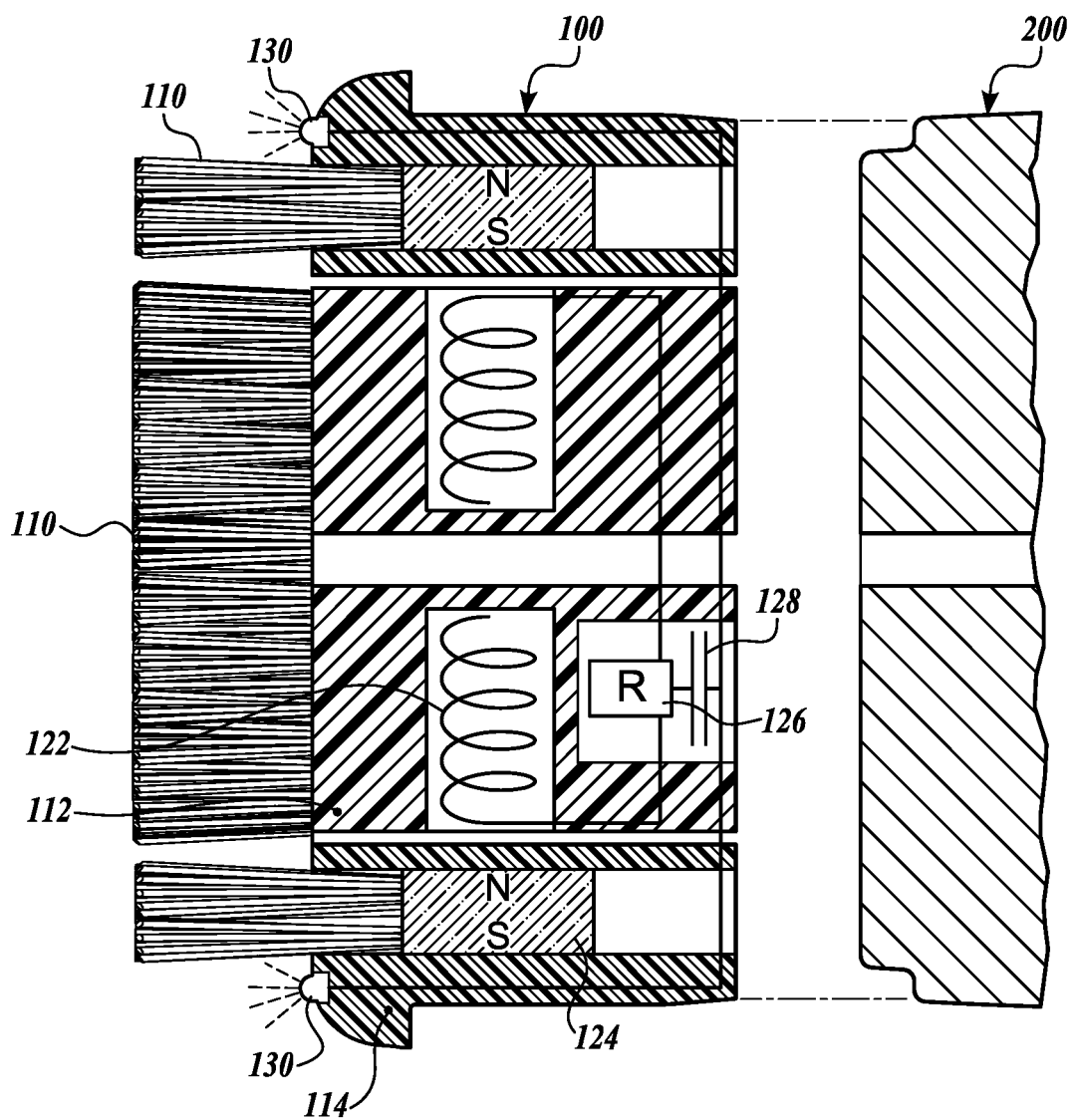
FIG. 3 is a cross-sectional side view of a skincare device in accordance with an embodiment of the present technology.

FIG. 3 is a cross-sectional side view of a skincare device in accordance with an embodiment of the present technology. In the illustrated embodiment, the magnets 124 are carried by the outer end effector structure 114, and the induction coils 122 are carried by the inner end effector structure 112. In operation, oscillations of the inner end effector structure 112 and/or of the outer end effector structure 114 cause inductive electrical current in the induction coils 122, which may be stored in the energy storage 128. In different embodiments, the energy storage 128 and/or other parts of the electrical circuitry are distributed through the inner end effector structure 112 and/or the outer end effector structure 114. The electrical energy stored in the energy storage 128 may be used to power the electrical devices 130. In other embodiments, the energy storage 128 may supplement electrical energy provided to the motor 310 or, in some embodiments, the energy storage 128 may, at least temporarily, provide all the power of the motor 310.

Figure 4:
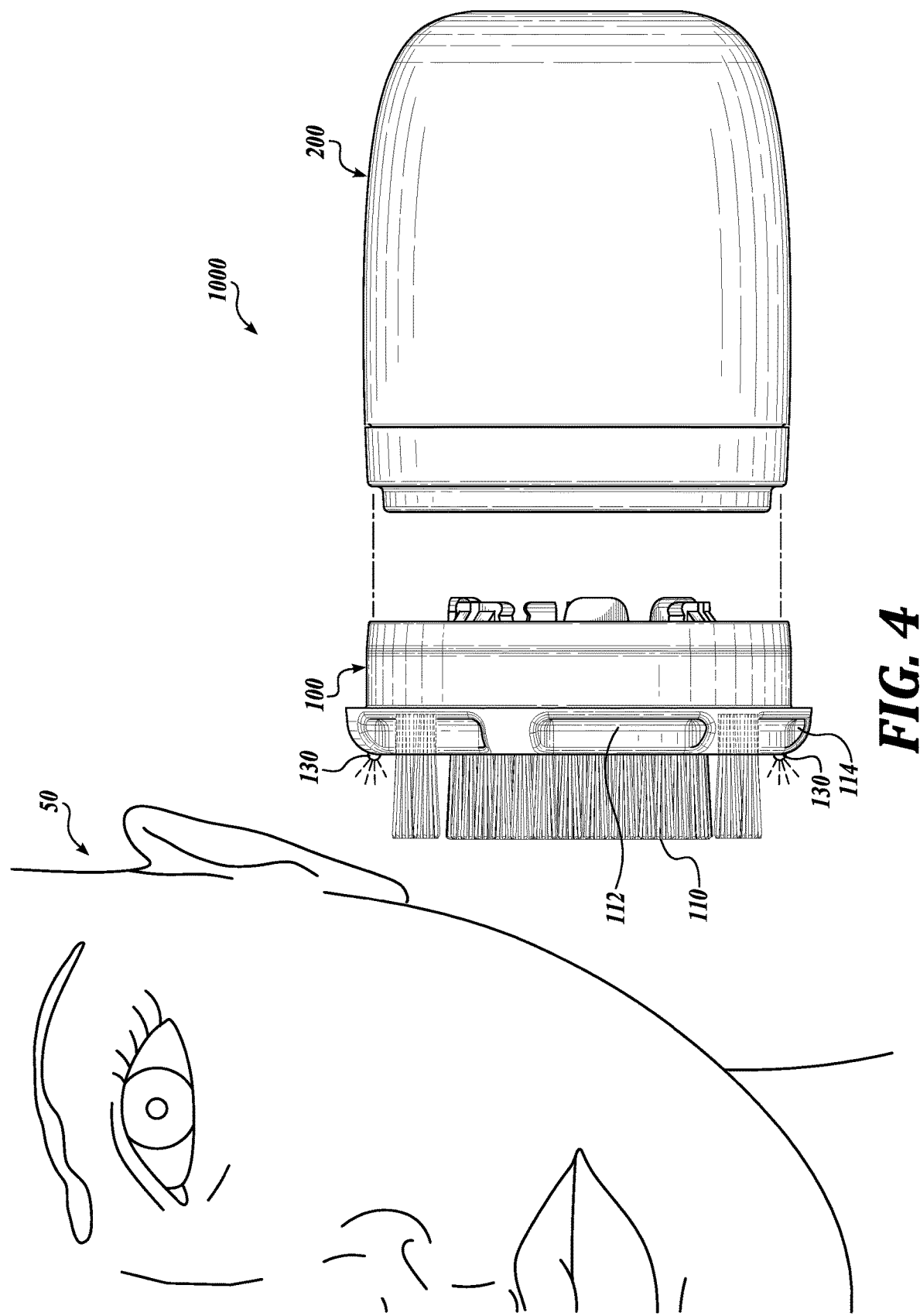
FIG. 4 is a side view of a skincare device in accordance with an embodiment of the present technology.

FIG. 4 is a side view of a skincare device 1000 in accordance with an embodiment of the present technology. The skincare device 1000 includes the end effector 100 and the handle 200. In the illustrated embodiment, the inner end effector structure 112 and the outer end effector structure 114 include contacting elements 110. However, in other embodiments, one or both of the inner end effector structure and the outer end effector structure carry elements other than the contacting elements 110, for example, the elements for massaging skin of user, for a thermal treatment of skin, for dispensing skin lotion, etc. As explained above, power for the electrical devices 130 may come from the energy generated by (harvested from) from the oscillatory motion of the inner/outer end effector structures, and stored in the energy storage 128.

Figure 5:
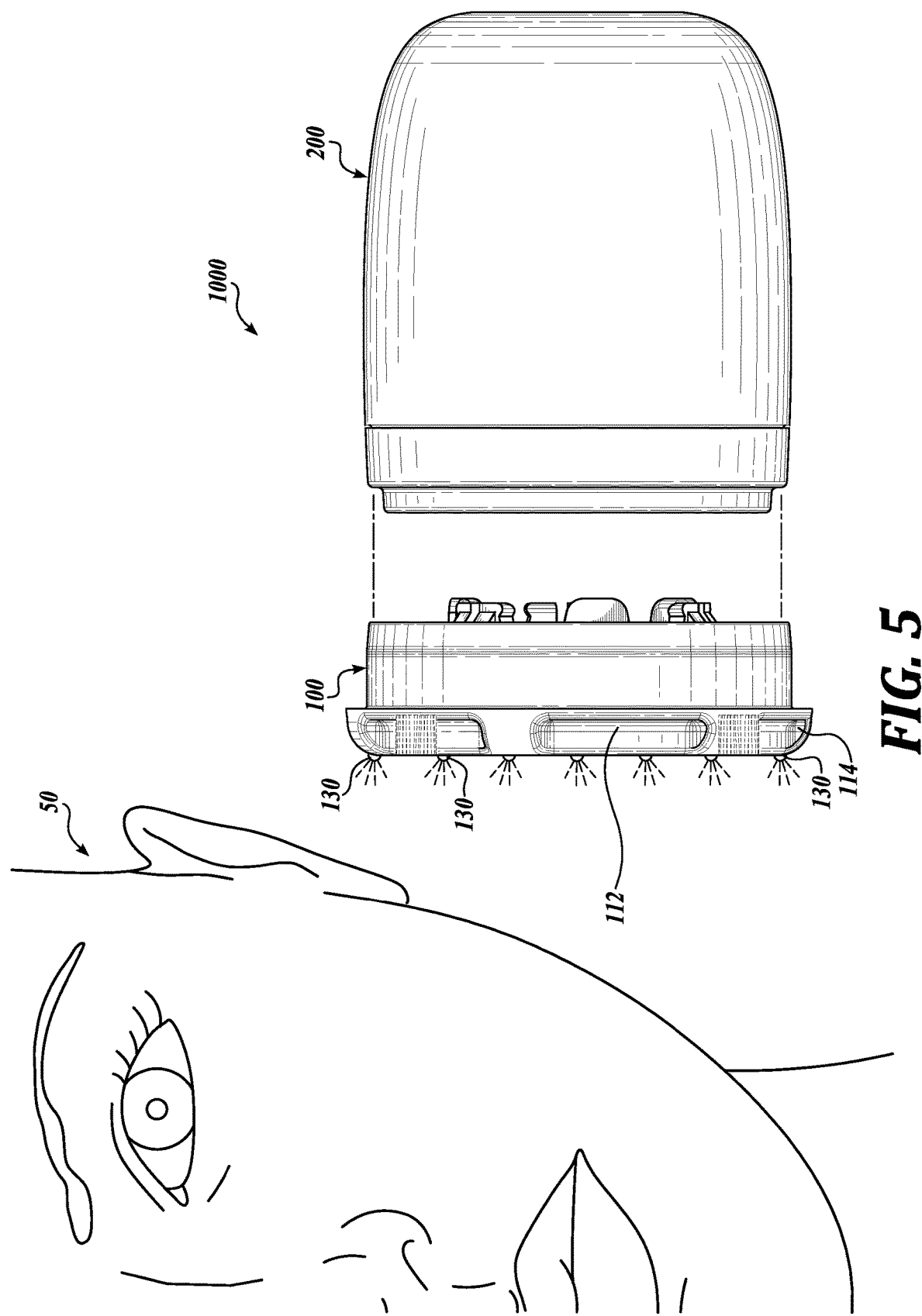
FIG. 5 is a side view of a skincare device in accordance with an embodiment of the present technology.

FIG. 5 is a side view of a skincare device 1000 in accordance with an embodiment of the present technology. In some embodiments, the end effector 100 does not carry the contacting elements 110. In the illustrated embodiment, the end effector 100 carries an array of the electrical devices 130. The electrical devices 130 (e.g., sources of light, heat, sound, ultrasound, motion, pressure, etc.) may be distributed over the inner end effector structure 112 and/or the outer end effector structure 114. Without being bound to theory, it is believed that sources of light, heat, sound, ultrasound, motion, pressure, etc., may have therapeutic effects or may result in increased pleasure for the user. Some or all of these devices may be energized from the energy storage 128 carried by the end effector 100.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. For example, in some embodiments the counter or controller may be based on a low-power buck regulator connected to a capacitor. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The invention claimed is:

1. An end effector, comprising:
    an inner end effector structure configured to oscillate about a first an axis, the inner end effector structure including at least one magnet and a plurality of contacting elements configured to contact skin of a user; and
    an outer end effector structure comprising at least one induction coil,
    wherein the at least one magnet and the at least one induction coil cooperate to generate electrical current in the at least one induction coil when the end effector oscillates about the axis,
    wherein the inner end effector structure is configured to oscillate with first oscillations about the axis, wherein the outer end effector structure is configured to oscillate with second oscillations about the axis, wherein the first oscillations of the inner end effector structure are generated by an oscillating shaft of the end effector, and wherein the second oscillations of the outer end effector structure are generated at least in part by electromagnetic interactions between the at least one magnet and the at least one induction coil.

2. The end effector of claim 1, wherein the first oscillations of the inner end effector structure and the second oscillations of the outer end effector structure are directed in opposite directions at least at some times during the operation of the end effector, and wherein the electrical current in the at least one induction coil increases with increased relative velocity between the at least one magnet of the inner end effector structure and the at least one induction coil of the outer end effector structure.

3. The end effector of claim 1, further comprising a regulator configured to regulate voltage of the induction coil into a charging voltage of an energy storage device carried by the end effector structure.

4. The end effector of claim 3, wherein the energy storage device is a capacitor.

5. The end effector of claim 3, wherein the energy storage device is a rechargeable battery.

6. The end effector of claim 3, further comprising an electrical device configured to receive electrical current from the energy storage device.

7. The end effector of claim 6, wherein the electrical device is configured to generate at least one of light, ultrasound, audible sound and heat toward the skin of the user.

8. The end effector of claim 6, wherein the electrical device is a light emitting diode (LED) configured to generate light toward the skin of the user.

9. The end effector of claim 1, wherein the plurality of contacting elements of the inner end effector structure is a first plurality of contacting elements, and wherein the outer end effector structure comprises a second plurality of contacting elements configured to contact the skin of the user.

10. A skincare device comprising the end effector of claim 1, the skincare device further comprising a handle connected with the end effector, wherein the handle comprises:
an electrical motor configured to impart oscillatory motion on an oscillating shaft connected with the inner end effector structure; and
a battery configured to power the electrical motor.

11. The A skincare device comprising the end effector of claim 3, the skincare device further comprising a handle connected with the end effector, wherein the handle comprises:
an electrical motor configured to impart oscillatory motion on an oscillating shaft connected with the inner end effector structure;
a battery configured to power the electrical motor; and
a controller configured to control at least one of the electrical motor and the energy storage device.

12. An end effector, comprising:
an inner end effector structure configured to oscillate about an axis, the inner end effector structure including at least one induction coil and a plurality of contacting elements configured to contact skin of a user; and
an outer end effector structure comprising at least one magnet,
wherein the at least one induction coil and the at least one magnet cooperate to generate electrical current in the at least one induction coil,
wherein the inner end effector structure is configured to oscillate with first oscillations about the axis, wherein the outer end effector structure is configured to oscillate with second oscillations about the axis, wherein the first oscillations of the inner end effector structure are generated by an oscillating shaft of the end effector, and wherein the second oscillations of the outer end effector structure are generated at least in part by electromagnetic interactions between the at least one magnet and the at least one induction coil.

13. The end effector of claim 12, wherein the plurality of contacting elements of the inner end effector structure is a first plurality of bristles, and wherein the outer end effector structure comprises a second plurality of bristles configured to contact the skin of the user.

14. The end effector of claim 12, further comprising a regulator configured to regulate voltage of the induction coil into a charging voltage of an energy storage device carried by the end effector structure.

15. The end effector of claim 14, wherein the energy storage device is a capacitor or a rechargeable battery.

16. The end effector of claim 15, further comprising an electrical device configured to receive electrical current from the energy storage device, wherein the electrical device is configured to generate at least one of light, ultrasound, audible sound and heat toward the skin of the user.

17. A skincare device comprising the end effector of claim 12, the skincare device further comprising a handle connected with the end effector, wherein the handle comprises:
an electrical motor configured to impart oscillatory motion on an oscillating shaft connected with the inner end effector structure; and
a battery configured to power the electrical motor.

18. An end effector comprising:
an inner end effector structure configured to oscillate about an axis, wherein the inner end effector structure comprises at least one magnet; and
an outer end effector structure comprising:
at least one induction coil, and
a plurality of electrical devices configured to affect skin of a user,
wherein the at least one induction coil and the at least one magnet cooperate to generate electrical current in the at least one induction coil, and wherein the electrical current at least partially powers the plurality of electrical devices,
wherein the inner end effector structure is configured to oscillate with first oscillations about the axis, wherein the outer end effector structure is configured to oscillate with second oscillations about the axis, wherein the first oscillations of the inner end effector structure are generated by an oscillating shaft of the end effector, and wherein the second oscillations of the outer end effector structure are generated at least in part by electromagnetic interactions between the at least one magnet and the at least one induction coil.

19. The end effector of claim 18, wherein the plurality of electrical devices is a first plurality of electrical devices, wherein the inner end effector structure comprises a second plurality of electrical devices configured to affect the skin of the user, and wherein the electrical current at least partially powers the second plurality of electrical devices.

20. The end effector of claim 19, wherein the first plurality of electrical devices and the second plurality of electrical devices comprise light emitting diodes (LEDs).

* * * * *